(12) United States Patent
Dyer

(10) Patent No.: US 11,331,784 B2
(45) Date of Patent: May 17, 2022

(54) ERGONOMIC HAND-HELD INSTRUMENT

(71) Applicant: Edward P. Dyer, Germantown, WI (US)

(72) Inventor: Edward P. Dyer, Germantown, WI (US)

( * ) Notice: Subject to any disclaimer, the term of this patent is extended or adjusted under 35 U.S.C. 154(b) by 0 days.

(21) Appl. No.: 16/870,191

(22) Filed: May 8, 2020

(65) Prior Publication Data
US 2021/0347033 A1 Nov. 11, 2021

(51) Int. Cl.
*B25G 1/10* (2006.01)
*B43K 23/008* (2006.01)
*A61B 17/3213* (2006.01)

(52) U.S. Cl.
CPC ............ *B25G 1/102* (2013.01); *B43K 23/008* (2013.01); *A61B 17/3213* (2013.01)

(58) Field of Classification Search
CPC ................................ B43K 23/008; B25G 1/102
See application file for complete search history.

(56) References Cited

U.S. PATENT DOCUMENTS

| D43,242 S | 11/1912 | Bernstein | |
|---|---|---|---|
| 1,188,394 A | * 6/1916 | Bernstein ................ | B43K 5/18 401/225 |
| 2,064,555 A | * 12/1936 | Mitchell .............. | A45D 40/026 401/59 |
| 3,055,341 A | 9/1962 | Riepe | |
| 3,947,977 A | * 4/1976 | Bishop ................... | G09B 11/02 434/166 |
| 3,986,403 A | 10/1976 | Hurd et al. | |
| 3,994,605 A | * 11/1976 | McKnight .............. | B43K 7/005 401/99 |
| 4,037,975 A | * 7/1977 | Huffman ................ | B43K 7/005 401/6 |
| D248,028 S | 5/1978 | Huffman | |
| 4,269,529 A | * 5/1981 | McCollough ............ | B43K 3/00 401/258 |

(Continued)

FOREIGN PATENT DOCUMENTS

WO WO1994/000305 1/1994
WO WO-9423956 A1 * 10/1994 ........... B43K 23/008

(Continued)

*Primary Examiner* — Jason W San
(74) *Attorney, Agent, or Firm* — Ryan Kromholz & Manion, S.C.

(57) ABSTRACT

An improved ergonomic hand-held instrument is provided with a housing having external surfaces defining contours which ergonomically engage surfaces of a user's thumb, index finger and middle finger when the user grasps the instrument, to provide a large surface area of contact between the user's hand and the instrument. The increased area of contact, compared to traditional designs, decreases the required level of applied unit area pressure, and also provides for greater control in manipulating the instrument by a wide range of users. The housing holds a removable cartridge having a working end or tip. The working end may be a pen, pencil, scalpel, knife, stylus, brush or similar tool. The top outer surface of the instrument includes an index finger compression surface for placement of the user's index finger. Base for storage of the instrument and at least one removable cartridge is also disclosed.

16 Claims, 7 Drawing Sheets

(56) References Cited

U.S. PATENT DOCUMENTS

| | | |
|---|---|---|
| 4,511,272 A | 4/1985 | Brown et al. |
| 4,572,227 A | 2/1986 | Wheeler |
| D292,297 S | 10/1987 | Bingham |
| 4,832,604 A * | 5/1989 | Rusk .................. G09B 11/02 401/6 |
| 4,896,543 A * | 1/1990 | Gullman ................ G01L 5/167 73/862.041 |
| 4,906,119 A | 3/1990 | Hartford et al. |
| 4,917,517 A * | 4/1990 | Ertz .................... B43L 15/00 401/48 |
| 5,037,224 A * | 8/1991 | Wright ................ B43K 23/04 401/48 |
| 5,143,463 A * | 9/1992 | Pozil .................. G09B 11/02 15/443 |
| 5,180,239 A | 1/1993 | Bistrack |
| 5,383,737 A | 1/1995 | Urion |
| D359,508 S | 6/1995 | Debbas |
| 5,470,162 A * | 11/1995 | Rubin ................... B43K 5/005 15/443 |
| 5,626,430 A | 5/1997 | Bistrack |
| 5,785,443 A | 7/1998 | Rubin |
| 5,853,210 A | 12/1998 | Robinson |
| 5,924,941 A * | 7/1999 | Hagey .................. A63B 60/14 473/551 |
| 5,984,795 A * | 11/1999 | Stafford ............ A63B 69/3632 473/206 |
| 6,043,807 A | 3/2000 | Carroll |
| 6,145,151 A * | 11/2000 | Herron ................. A46B 5/02 15/143.1 |
| 6,158,910 A * | 12/2000 | Jolly .................... B25G 1/102 16/430 |
| 6,250,828 B1 | 6/2001 | Liu |
| 6,254,293 B1 * | 7/2001 | Citrenbaum ......... B43K 23/008 30/340 |
| 6,315,476 B2 * | 11/2001 | Nakagawa ............ B43K 5/005 401/6 |
| 6,328,494 B1 | 12/2001 | Moxon |
| 6,343,885 B1 * | 2/2002 | Heyne ................. B43K 7/005 16/430 |
| D462,090 S | 8/2002 | Debbas |
| 6,554,515 B2 | 4/2003 | Debbas |
| D477,700 S | 7/2003 | Chezzi |
| 6,637,962 B1 | 10/2003 | Roche et al. |
| 6,681,830 B1 * | 1/2004 | Vulpitta ............ B65D 73/0007 156/523 |
| 6,795,057 B2 | 9/2004 | Gordon |
| 6,908,245 B1 * | 6/2005 | Schulken ............ B43K 23/004 15/443 |
| D508,716 S | 8/2005 | Bhavnani |
| 6,988,295 B2 | 1/2006 | Tillim |
| 7,128,484 B2 | 10/2006 | Schulken |
| D553,188 S | 10/2007 | DaBoll |
| D566,182 S | 4/2008 | Snyder et al. |
| 7,384,207 B2 * | 6/2008 | Bhavnani ............. A46B 5/02 401/109 |
| 7,484,903 B2 | 2/2009 | Komorowski |
| 7,523,525 B2 * | 4/2009 | Lawless ................. B25B 33/00 16/430 |
| D610,614 S | 2/2010 | Dyer |
| D611,540 S | 3/2010 | Li |
| 7,758,455 B2 * | 7/2010 | Thomas ................ A63B 60/10 473/459 |
| D621,403 S * | 8/2010 | Agnitti ................... D14/411 |
| 7,930,804 B2 * | 4/2011 | Cornfield .............. B25G 1/102 16/430 |
| 8,092,411 B2 * | 1/2012 | Betcher ................ A61F 5/0118 602/21 |
| 8,152,395 B2 * | 4/2012 | Liu ...................... B43K 23/004 401/6 |
| 8,156,610 B2 | 4/2012 | McKenzie et al. |
| 8,182,165 B2 * | 5/2012 | Lee ........................ G09F 19/08 401/117 |
| D667,054 S * | 9/2012 | Dyer ........................... D19/178 |
| D700,909 S | 3/2014 | Bowser |
| D701,861 S | 4/2014 | Foster et al. |
| D710,942 S * | 8/2014 | Pincus ....................... D19/203 |
| D742,381 S | 11/2015 | Joseph |
| D766,371 S | 9/2016 | Wiseman et al. |
| D774,512 S | 12/2016 | Liu |
| 9,522,562 B2 | 12/2016 | Cho et al. |
| 9,610,797 B2 * | 4/2017 | Boisdevesys ......... B43K 24/06 |
| 9,764,590 B2 | 9/2017 | Lowrey, Jr. |
| D806,796 S | 1/2018 | Cowen et al. |
| D809,061 S | 1/2018 | Wong et al. |
| D839,349 S | 1/2019 | Cowen et al. |
| D847,259 S | 4/2019 | Lozano et al. |
| D855,700 S * | 8/2019 | Cowen ...................... D19/178 |
| D863,438 S | 10/2019 | Chen |
| 2001/0001630 A1 | 5/2001 | Nakagawa |
| 2002/0034411 A1 * | 3/2002 | Rusk ..................... B43K 23/008 401/6 |
| 2006/0083575 A1 * | 4/2006 | Kim ...................... B43K 23/008 401/6 |
| 2006/0174448 A1 | 8/2006 | You |
| 2007/0020021 A1 | 1/2007 | Snyder et al. |
| 2007/0196158 A1 | 8/2007 | Roche et al. |
| 2007/0298388 A1 | 12/2007 | DaBoll |
| 2010/0095487 A1 * | 4/2010 | Gitman ................ B43K 23/008 16/430 |
| 2011/0064510 A1 | 3/2011 | Shultz |
| 2012/0003026 A1 * | 1/2012 | Geddes ................ B43K 21/003 401/85 |
| 2012/0027500 A1 * | 2/2012 | Jun ........................ B43K 8/003 401/258 |
| 2013/0061725 A1 * | 3/2013 | Freuler .................. B25G 1/102 81/489 |
| 2013/0192028 A1 | 8/2013 | Pierce |
| 2014/0219702 A1 * | 8/2014 | Pincus ................. B43K 23/008 401/6 |
| 2015/0279229 A1 | 10/2015 | Padden |
| 2015/0352891 A1 * | 12/2015 | Provda ................ B43K 23/004 401/7 |
| 2016/0159139 A1 * | 6/2016 | Vadenne ................ B43M 11/06 118/77 |
| 2016/0229219 A1 | 8/2016 | Pincus |
| 2017/0143954 A1 * | 5/2017 | Messina ................... G09B 5/00 |
| 2018/0281166 A1 * | 10/2018 | Chmelar ................. B25B 13/06 |
| 2019/0054757 A1 * | 2/2019 | Somers ................. B43K 23/012 |
| 2020/0009900 A1 | 1/2020 | Kaiser et al. |
| 2020/0023668 A1 * | 1/2020 | Elliot ................... B43K 23/008 |

FOREIGN PATENT DOCUMENTS

| | | |
|---|---|---|
| WO | WO2006/131068 | 12/2006 |
| WO | WO2009/033367 | 3/2009 |
| WO | WO2018/078364 | 5/2018 |

* cited by examiner

ERGONOMIC HAND-HELD INSTRUMENT

FIELD OF THE INVENTION

The present invention is directed to an ergonomic instrument to be held in one's hand, as might be typically used for writing, with a readily removable cartridge and a separate stand. Examples of such instruments include writing instruments such as pens and pencils, cutting instruments such as knives, awls, scalpels, and scribes, computer-related devices such as styluses, and other hand-held instruments such as brushes, cosmetics applicators, etc.

BACKGROUND OF THE INVENTION

In the past, traditional hand-held instruments, such as those commonly used for writing, have generally been provided with a cylindrical shaft which is manipulated by the thumb and index finger of the user acting in conjunction with each other to control the tip of the device so as to accomplish a specified task. Examples of such traditional single tip hand-held instruments are writing instruments such as pens and pencils, cutting instruments such as knives and awls, tools such as scribes, painting instruments such as brushes, cosmetics application equipment and digitalizing contacting devices such as computer styluses. During their use, the surface of such traditional instruments contacts a relatively small surface area of the user's hand.

Historically, improvements to such traditional hand-held instruments concerned the mechanical aspects of the devices, such as new inks, ink flow mechanisms and delivery of the ink to the writing surface. A fundamental disadvantage of traditional instruments is that they have only a single rigidly mounted working tip and the ubiquitous cylindrical shaft does not conform well to the surfaces of the user's fingers, palm or closed inner hand.

One of the least developed areas of hand-held instrument design is the relationship between the grasping shape of the instrument and the natural shape of the user's hand. This has a significant effect on the user's comfort and ability to control and manipulate the instrument, particularly when the instrument is to be used for a prolonged period of time. The traditional hand-held instrument possesses a tubular or nearly tubular design with a cylindrical cross-section or nearly cylindrical cross-section, requiring the user to conform the user's hand to the pen design. Traditional instruments therefore contact a relatively small proportion of the surface area of the user's fingers, leaving a large area of the thumb and fingers unused. Further, the bulk of the user's hand is not used to dissipate the physical stress that accompanies the use of the hand-held instrument. The use of convention instruments causes discomfort and cramping for the user. Further, the rigid surfaces of the instrument exert pressure (in the form of negative leverage) and friction on the user's fingers. For an elderly user, this discomfort is often exacerbated. Thus, it is advantageous that a larger percentage of the surface area of the hand and fingers which work with a hand-held instrument should contribute to controlling the hand-held instrument.

Prior attempts were made to modify hand-held instruments to reduce discomfort and fatigue. For example, instruments have been produced which have soft rubber coating materials. However, such materials tend to reduce the control of the instrument in the hand. Also, it has been proposed to provide hand-held instruments with different concave surfaces. However, these concave surfaces have not overcome the basic problems arising from the basic idea of a cylindrical shaft oriented to extend in a direction between the thumb and index finger of the user and out away from the hand. The user of a cylindrical style pen has to conform the hand to the pen. Further, the prior art clearly the evidences the struggle to promote the use of all available ink in a pen.

SUMMARY OF THE INVENTION

The present invention is directed to providing an ergonomic hand-held instrument with a removable cartridge and a retractable working tip. A separate stand for the instrument and removable cartridges is also disclosed.

Another object of the invention is to provide an ergonomic hand-held instrument which can be held with a high degree of comfort for long periods of time with reduced fatigue of the hand. The present invention will provide an ergonomic hand-held instrument which provides less friction and pressure on the contacting surfaces of the hand, thereby reducing the development of blisters or calluses on the fingers or hand, for example, along the middle finger which results from friction and pressure during extended use.

Another object of the invention is to provide an ergonomic hand-held instrument which allows for performing manual activity with a high degree of precision. The present invention provides an ergonomic hand-held instrument which provides a greater proportion of its surface in contact with the user's hand, thus enabling a greater degree of control and manipulation while simultaneously providing for greatly increased comfort. Therefore, the invention conforms to the hand of the user. Further, the invention provides for a right-handed and left handed embodiment to accomplish the high degree of precision.

Another object of the present invention is to position the end or tip of the pen in a substantially vertical position promoting movement of ink in the pen towards the tip.

The present invention accomplishes these and other objectives by providing a hand-held instrument which has a cartridge, cartridge assembly, with a working tool, such as a pen or pencil, which extends and retracts from an ergonomically shaped clam shell housing, with the clam shell housing preferably having a forward surface and an opposing rearward surface, first and second curved side surfaces, a generally convex upper surface and a generally concave lower surface. The cartridge is removably positioned within a cartridge container. The cartridge container comprises a cartridge adapter and an advance button. The invention provides for a first embodiment of the cartridge adapter, and a second embodiment of the cartridge adapter. Where the second embodiment of the cartridge adapter comprises at least one longitudinal ridge reducing resonance of a concentric spring about the cartridge container. The longitudinal ridge benefit of reduced resonance of a concentric spring of the internal components occurs during extension of the working tool of the cartridge beyond the forward surface of the ergonomically shaped clam shell housing. The second embodiment of the cartridge adapter further comprises at least one circumferential ridge to provide positional stability between the cartridge adapter and the advance button removably coupled with the cartridge adapter. The top portion of the clam shell housing is ergonomically contoured so as to be fitted with the index finger of a user. A novel index finger compression surface is provided for greater comfort and control. One of the side surfaces is adapted to engage the thumb of a user and the other is adapted to engage the middle finger of the user. The forward surface is oriented so that in use the instrument extends in a direction which is further ahead of the user's index fingertip. The instrument is of sufficient size so that it fits comfortably against the palm, such that the instrument provides a greater conformation with the contours of the thumb, index and middle fingers of the hand. In so doing, a relatively large contact area exists between the hand and the instrument. The increased area of contact decreases the pressure at any given point of contact, and the increased area of contact also allows for greater control of the instrument. The instrument of the present invention may be advantageously used in multiple manually performed activities utilizing hand-held instruments, including for example, writing, cutting, painting, surgery, cosmetics application, etc. by simple replacement of the removable cartridge.

Specifically, the present invention provides for an ergonomic hand-held instrument, comprising: a shell having a shell body defined by a front and an opposed rear; a convex top is positioned from the front to the rear; two oppositely opposed sides are positioned between the front and the rear; and the front provides for a device tip.

The present invention further provides the shell has an asymmetric shape. The asymmetric shape provides for the ergonomic hand-held instrument conforming to a user's hand. The present invention further provides the convex top comprises a compression surface in communication with the shell body, wherein the compression surface has a hardness less than said shell body and is easily compressible and conformable by the index finger. The present invention further provides the compression surface provides for placement of an index finger. The asymmetric shape, convex top and compression surface of the ergonomic hand-held instrument provide a contact surface having a larger area as compared to a user's hand contact surface with a conventional instrument. The increased contact surface between the user's hand and the ergonomic hand-held instrument, as compared to that of a conventional instrument, provides for reduced hand stress, strain and cramping of a user of the ergonomic hand-held instrument as compared to the hand stress, strain and cramping of a user of the conventional instrument.

The present invention further provides for a cartridge assembly having the device tip and positioned at least partially within a cavity defined by the shell; a guide tip about the cartridge assembly and frictionally supported within the cavity; the cartridge assembly is slidably positionable at least partially beyond the rear, through a first opening of said rear; the cartridge assembly is slidably positionable beyond the front, through a second opening of the front.

The present invention further provides the cartridge assembly is an interchangeable cartridge assembly; the interchangeable cartridge assembly is a quick-change cartridge assembly; the cartridge assembly is positioned within a cartridge container; an o-ring is about the cartridge assembly providing for an impact dampening; the cartridge container having at least one ridge along a cartridge container outer surface, wherein the ridge frictionally minimizes a resonance of a concentric spring, maintaining a lateral position of the spring; and the cartridge container is rotationally positioned to provide for an extension of the device tip.

The present invention further provides the device tip comprises at least one of a pen, a stylus and a cutting tool; further comprises a base for storage of the shell; and a first button is positioned through the shell to provide for a retraction of the device tip.

The present invention will satisfy the above described needs yet it is an improved design over previous ergonomic designs because, among other features, it incorporates a retractable working tool or tip mechanism. Having the capability to retract the tip provides the user with the ability to safety carry the instrument in a pocket or other clothing article. With the tip retracted, ink would not leak onto clothing or cause inadvertent marking of clean surfaces. Moreover, if the instrument is configured as a hard-tipped stylus, cutting tool, or other sharp pointed article, the user would now be able to retract the point to have a safe instrument for transport storage or other use when exposure of the sharp tip is not required.

Other objects, advantages and features of the present invention will be more readily appreciated and understood when considered in conjunction with the following detailed description and drawings.

Figure 1:
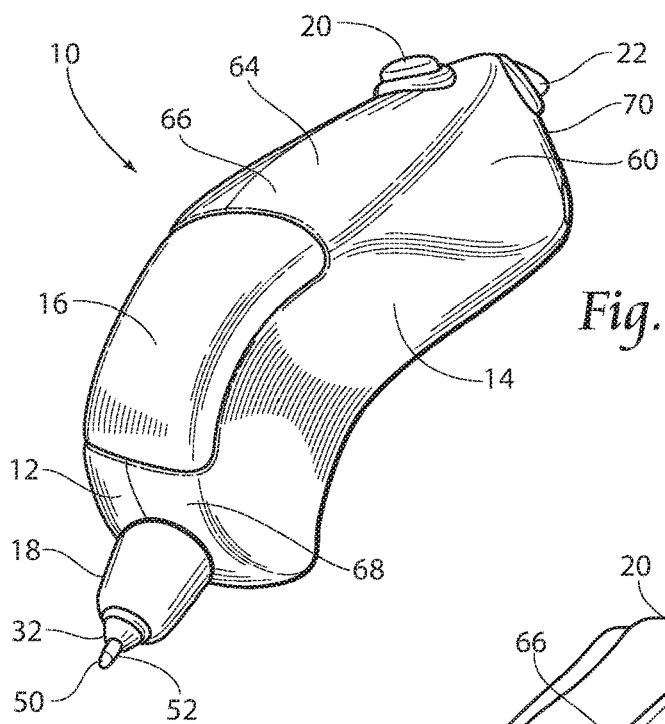
FIG. 1 is a perspective view of a first embodiment of an improved hand-held instrument, according to the present invention with the working tool or tip extended.

It is understood that FIGS. 1-18 represent a right-hand orientation embodiment of the invention. It is understood that FIG. 19 represents a left-hand orientation embodiment of the invention.

DESCRIPTION OF THE PREFERRED EMBODIMENT

The purpose of the improved ergonomic hand-held instrument (10, 10') described by the present invention is to provide an interchangeable working tool or tip 50 for the user. In the illustrated embodiment of FIGS. 1-12, an ink pen tip 52 is shown as the working tool 50 incorporated in a removable cartridge assembly 30. However, the working tool 50 can include any one of a number of devices which require precise manual control. Referring to FIG. 13, examples include other writing instruments such as pencils, felt tip markers and fountain pens 52, a blade for a cutting 54 or a computer screen contacting device such as a computer stylus 56.

Figure 2:
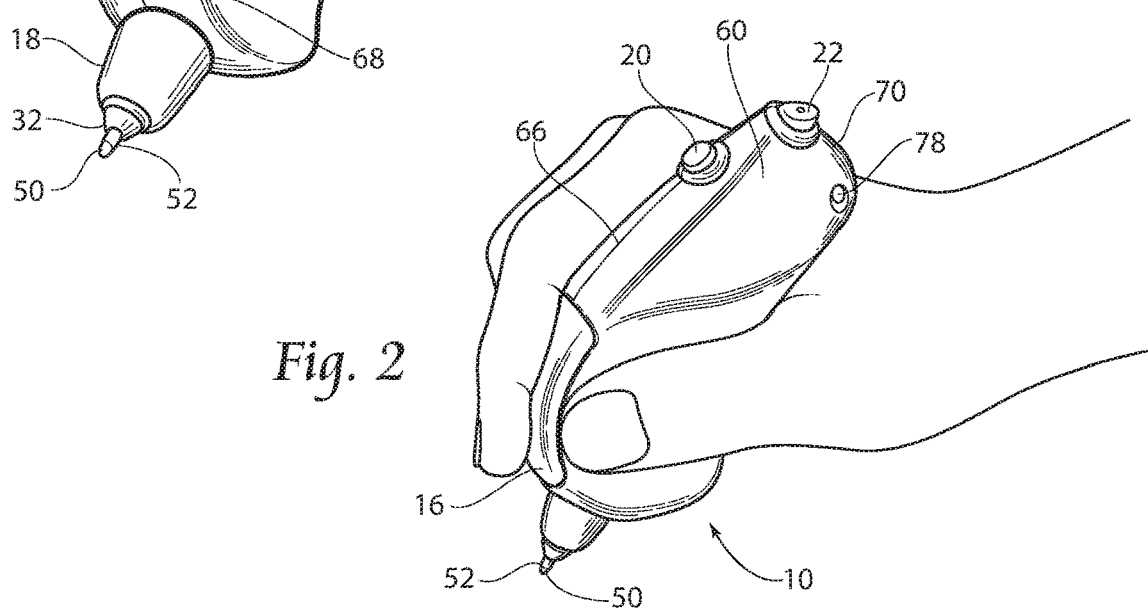
FIG. 2 is a perspective view of the first embodiment of the improved hand-held instrument according to the present invention conforming to a user's hand in the use position.

In my preferred embodiment, as shown in FIGS. 1 and 2, the assembled clam shell housing 60 of a first embodiment of the hand-held instrument 10 is constructed of two mating pieces, the first or right clam shell housing 12, and the second or left clam shell housing 14. These two housing pieces 12, 14 are attached or bonded during the assembly process through common methods, such as snap fitting tabs, sonic welding or adhesive. Each of these pieces 12, 14 has an inner surface 62 and an outer surface 64. In use, the outer surface 64 of the first or right clam shell housing 12 is engaged by the middle finger of a right-handed user and the outer surface 64 of the second or left clam shell housing 14 is engaged by the thumb of the user. The top surface 66 is engaged by the user's index finger. An index finger compression surface 16 is provided in the housing top surface 66. The compression surface 16 is in communication with the clam shell housing 60. The compression surface 16 has a hardness less than the remainder of the top surface 66 and the clam shell housing 60. In this preferred embodiment, the outer surfaces 64 have contours which are smooth and gradual, without sharp edges. Similarly, the two mating clam shell housing pieces 12, 14 of the instrument 10 are joined smoothly. A high quality finish may be applied to the entire housing 60. These features enhance the level of comfort for the user of the instrument 10.

Figure 3:
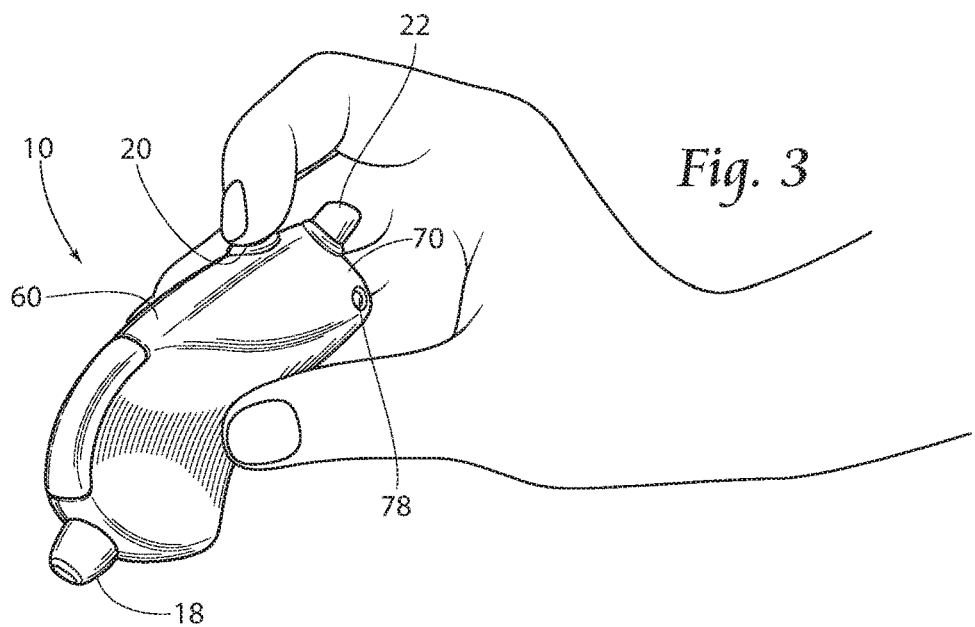
FIG. 3 is a perspective view of the first embodiment of the improved hand-held instrument with a retraction button depressed.
Figure 4:
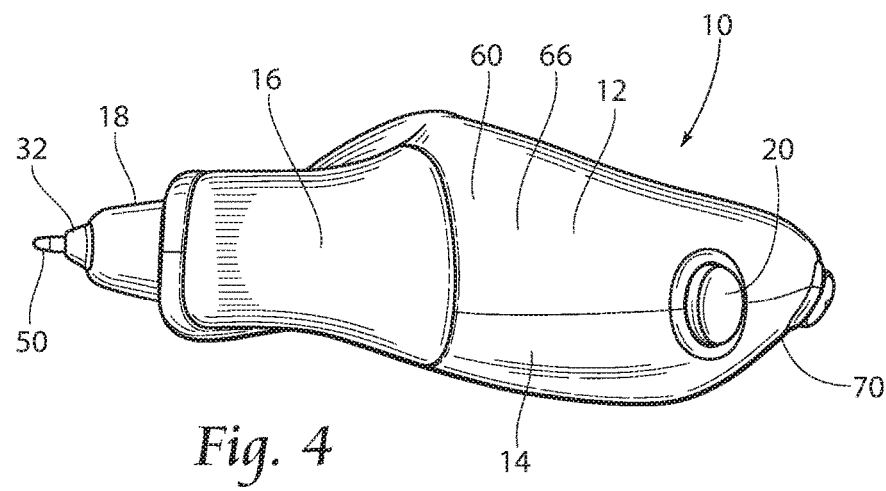
FIG. 4 is a top plan view of the first embodiment of the improved hand-held instrument with the working tip extended, as shown in FIG. 1.
Figure 5:
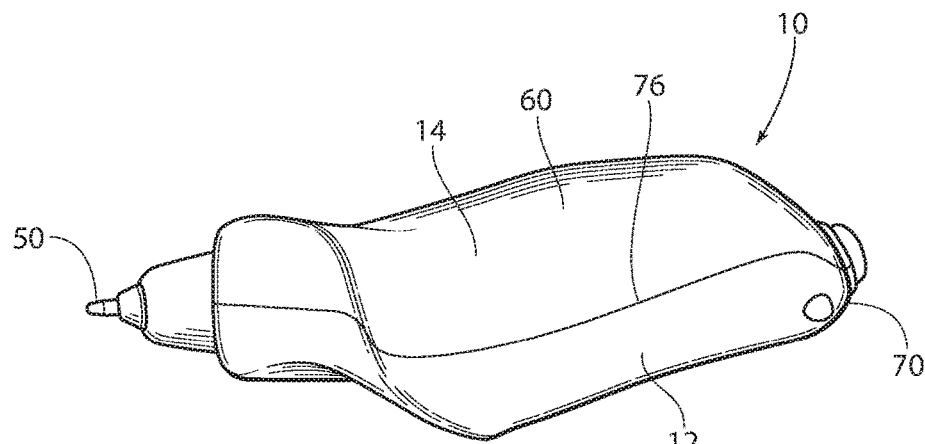
FIG. 5 is a bottom plan view of the first embodiment of the improved hand-held instrument.
Figure 6:
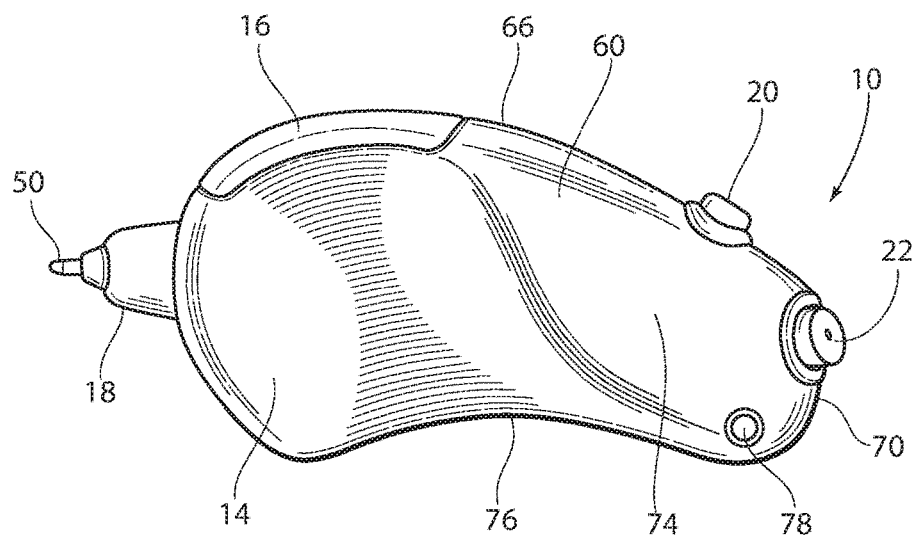
FIG. 6 is a left side view of the first embodiment of the improved hand-held instrument.
Figure 7:
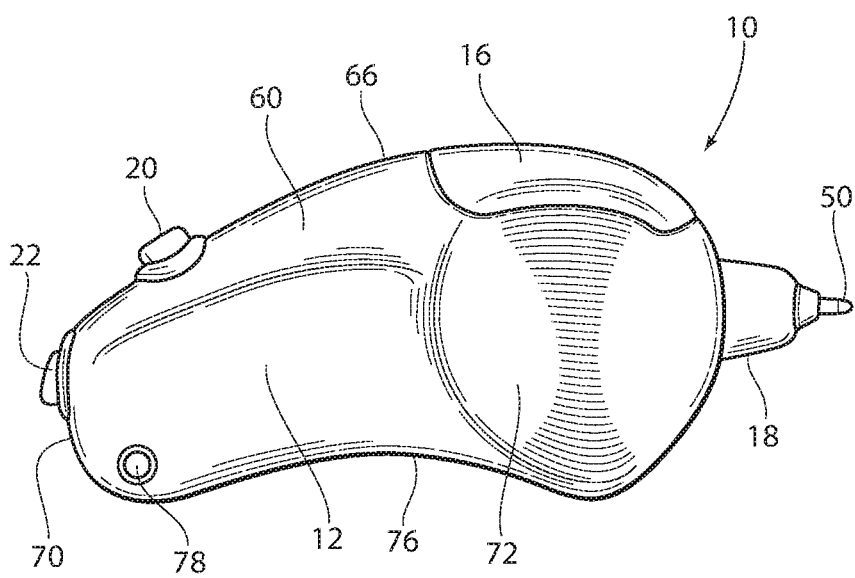
FIG. 7 is a right side view of the first embodiment of the improved hand-held instrument.
Figure 8:
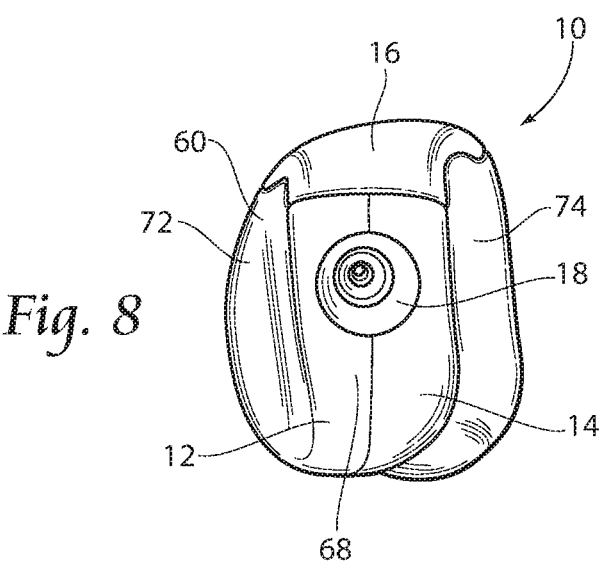
FIG. 8 is a front elevation view of the first embodiment of the improved hand-held instrument.
Figure 9:
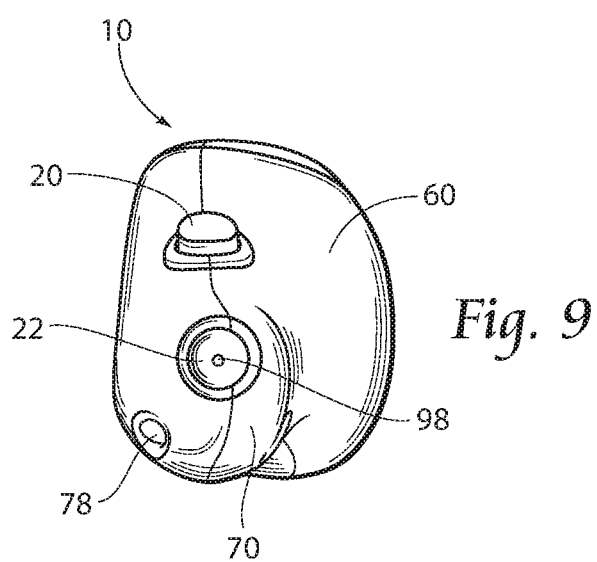
FIG. 9 is a rear elevation view of the improved hand-held instrument.

More specifically, as shown in FIGS. 1-9 of my preferred embodiment, the outer surfaces 64 define a smooth ergonomic shape having a forward surface 68 and an opposed rearward surface 70, and a first side surface 72 and an opposed second side surface 74 which are contiguous and generally perpendicular to the forward and rearward surfaces 68 and 70. Further defined is a bottom surface 76 and the aforementioned top surface 66. The top surface 66 has a generally convex shape, as best seen in FIGS. 1 and 2. The bottom surface 76 has a generally concave surface as shown in FIGS. 6 and 7. The top surface 66 is further contoured such that the user would typically place his or her index finger thereon at the index finger compression surface 16 formed or installed therein. In addition, the third finger may also rest the second side surface 74 proximate the location of the middle finger (not shown). Furthermore, the rearward surface 70 also may have an opening 78 as best shown in FIGS. 2, 3 and 6 for receiving an optional lanyard (not shown). The placement of the thumb, index finger and middle finger (plus third finger) as described permits the user to comfortably grip the improved instrument 10, yet hold the instrument in a manner quite conducive to accurate and precise positioning of the working end or tip 50 of the instrument. Thus, the present invention 10 in use permits the hand of the user to assume a comfortable arched configuration. Further, as illustrated in FIG. 2, the present invention 10 positions the end or tip 50 of the pen 52 in a substantially vertical position promoting movement of ink in the pen 52 towards the tip 50. Further, as illustrated in FIG. 2, the invention 10 conforms to the hand of the user which is opposite that of the prior art.

Figure 10:
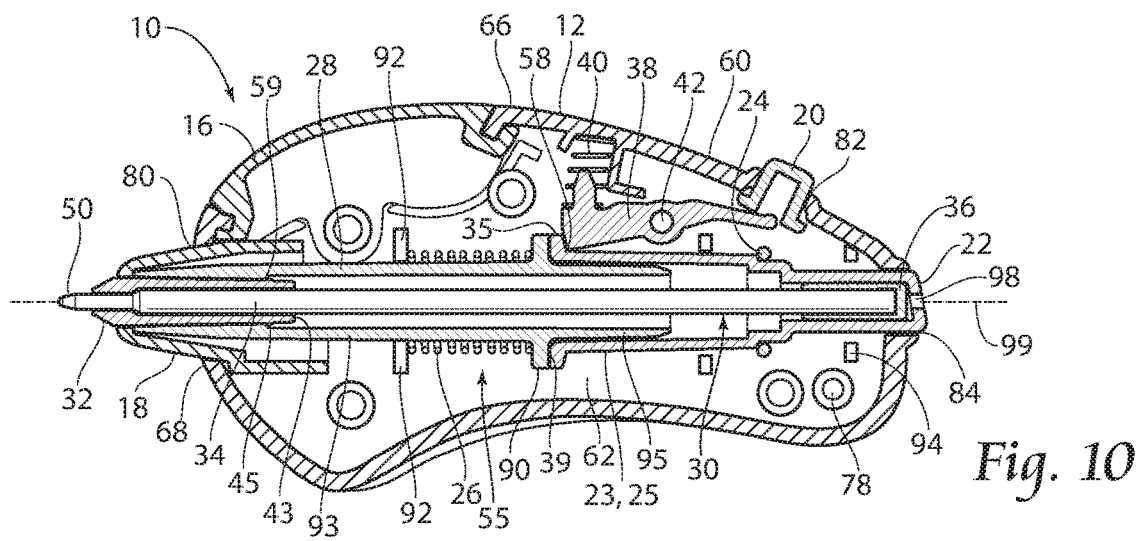
FIG. 10 is a sectional view of the improved hand-held instrument, further comprising a first embodiment of a cartridge adaptor, with the working tool or tip extended.
Figure 11:
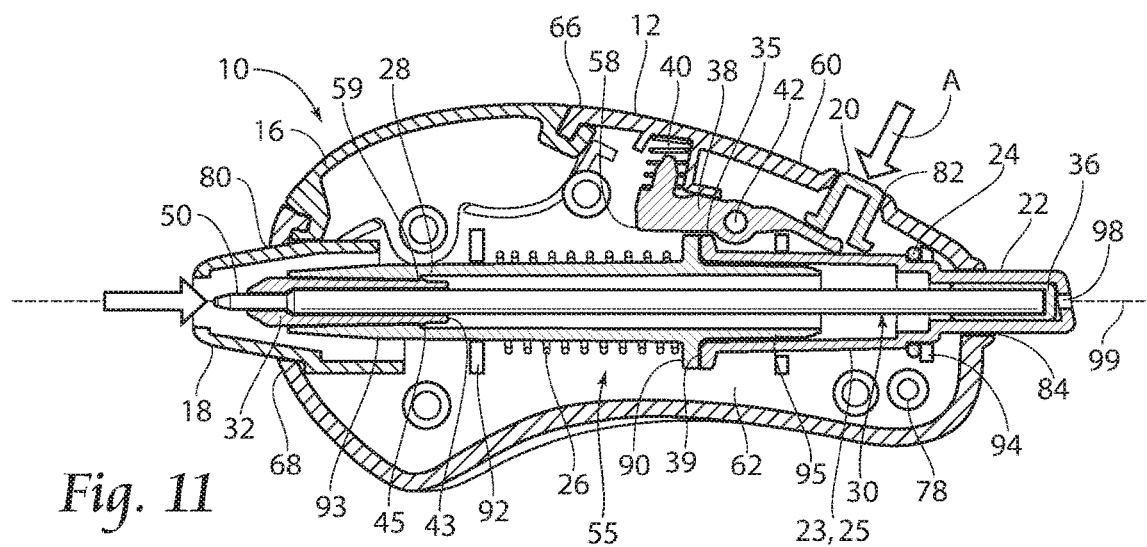
FIG. 11 is a sectional view of the improved hand-held instrument, further comprising the first embodiment of the cartridge adaptor, with the working tool or tip retracted.

Referring to FIGS. 10 and 11, a sectional view of a hand-held instrument 10 according to the present invention is shown. As previously discussed, the first clam shell housing piece 12 and the second clam shell housing piece 14 of the hand-held instrument 10 fit together to form the clam shell housing 60. Generally speaking, the housing pieces have been separated in the view of FIGS. 10 and 11. The cartridge assembly 30 may be located anywhere within the clam shell housing 60 and extend from any portion of the clam shell housing forward surface 68. A tip or tool 50 extends from the cartridge assembly 30 at the clam shell housing forward surface 68 and through opening 80. In a preferred embodiment, the cartridge assembly 30 contains a pen cartridge having an ink tip 52. The clam shell housing 60 according to the present invention 10 includes a finger grip 16 mounted in or to the top surface 66 of the housing 60. A tip guide 18 projects through the opening 80 in the housing 60. A retraction button 20 projects through another opening 82 in the top surface 66 of the housing 60. An advance button 22 projects through a third opening 84 in the housing 60. A first embodiment of a cartridge adapter 28 nestled within the advance button 22 is positioned between the tip opening 80 and the advance opening 84. Specifically, the cartridge adaptor 28 comprises a cartridge adaptor proximal section 93, which extends towards the tip guide 18, and a cartridge adaptor distal section 95, which extends towards the advance opening 84, where the proximal section 93 and distal section 95 are separated by a circumferential rib 90 of the cartridge adaptor 28. The combination of the cartridge adapter 28 and the advance button 22 comprises a cartridge container 55.

In the case of an ink pen or tip 52, the removable cartridge assembly 30 includes a tip guide 32, an ink reservoir 34 and a vented plug 36. In a preferred embodiment, the cartridge assembly 30 is cylindrical and elongated. However, the cartridge assembly 30 can be any shape (including square, oblong, conical, etc.) and need not be elongated.

A coil spring 26 rests between the circumferential rib 90 on the adapter cartridge 28 and an abutment 92 on the interior surface 62 of the housing 60. The spring 26 biases the cartridge adapter 28 in an inward direction relative to the opening in the tip guide 18.

A release latch or lever 38 pivots on a latch shaft 42 which is supported in an opening formed on the inner surface 62 of the housing. One end of the latch is biased inwardly relative to the housing 60 by means of a latch spring 40 located between the latch 38 and the inner surface 62 of the housing. The distal end of the latch 38 contacts the retraction button 20 that protrudes through opening 82 in the housing 60. The retraction button 20 in the preferred embodiment is generally cylindrical with an oblong cross section. Alternatively, the retraction button 20 is generally cylindrical with a circular cross section. Its inboard end includes outward extending tabs (or a ridge), on two opposing sides to permit the button 20 to extend outward from the assembled clam shell housing 60 but still be retained within the clam shell housing by the tabs or ridge.

As best shown in FIG. 10, the latch 38 has an end 58 proximate to the latch spring 40 and distal from the retraction button 20; the end 58 engages with a release ledge 35 on the end of the advance button 22 to maintain the tool or tip 50 in the extended position (as shown). Now referring to FIG. 11, when the retraction button 20 is depressed (as shown by the arrow A), the release latch end 58 disengages from the advance button 22 and the spring 26 biases the cartridge assembly 30 to its retracted position. A dampening O-ring 24 is situated about a step in the advance button 22 and contacts a second abutment 94 on the interior surface 62 of the housing 60 to absorb the impact of the retracting cartridge assembly 30, adapter cartridge 28 and advance button 22.

Figure 12:
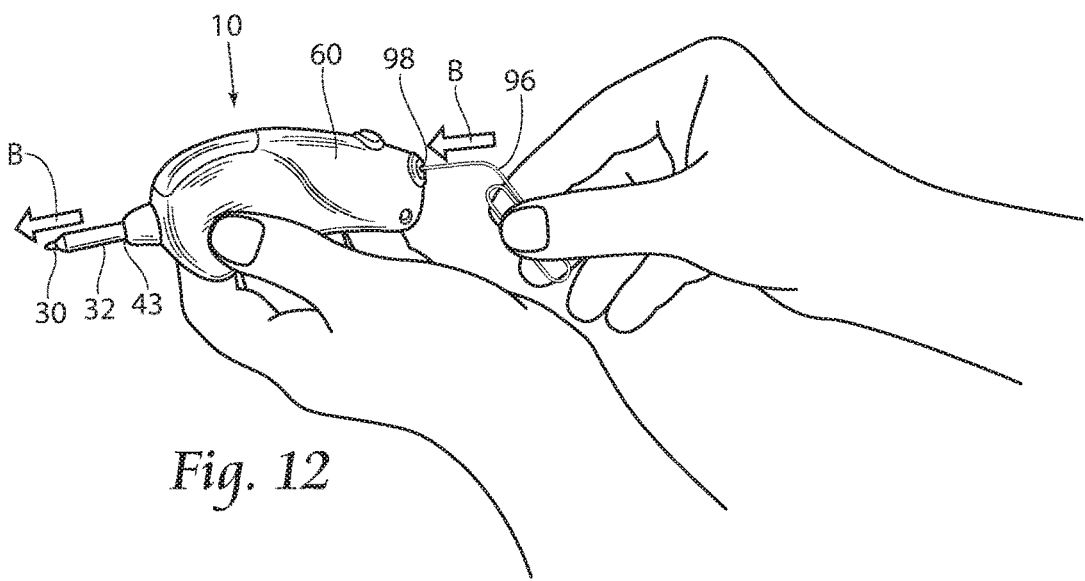
FIG. 12 is a perspective view of the first embodiment of the improved hand-held instrument according to the present invention being grasped by a user's hand in the cartridge change position and a tool being used by the other hand to eject the cartridge.
Figure 13:
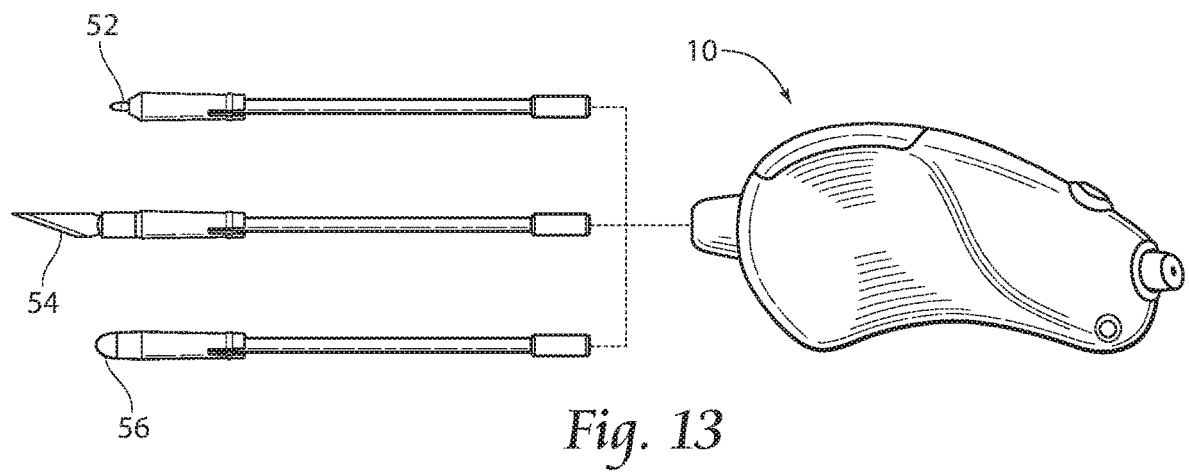
FIG. 13 is a perspective view of the improved hand-held instrument according to the present invention with three exemplary working tools or tips attached to removable cartridges.

Now referring to FIG. 12, it can be seen that a simple extraction tool 96 may be placed in a small opening 98 formed in the advance button 22 for purposes of removing the working tool or tip 50 from the instrument 10. Advancing the tool 96 in the direction of arrows B ejects the cartridge 30 from the instrument 10. A replacement cartridge 30 may be installed in the instrument 10 by simply sliding it through the opening formed in tip guide 18 until the cartridge is firmly seated within the instrument. As again shown in FIG. 13, the working tool or tip 50 can take the form of numerous devices. Those shown, including pen 52, knife 54 and stylus 56, are for illustration purposes only and are not meant to limit the scope or application of the present invention 10.

Figure 14:
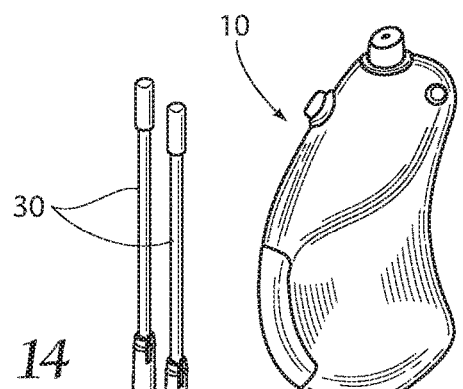
FIG. 14 is a partially exploded perspective view of the improved hand-held instrument being placed in the base and removable cartridges according to the present invention optionally placed in the base.
Figure 15:
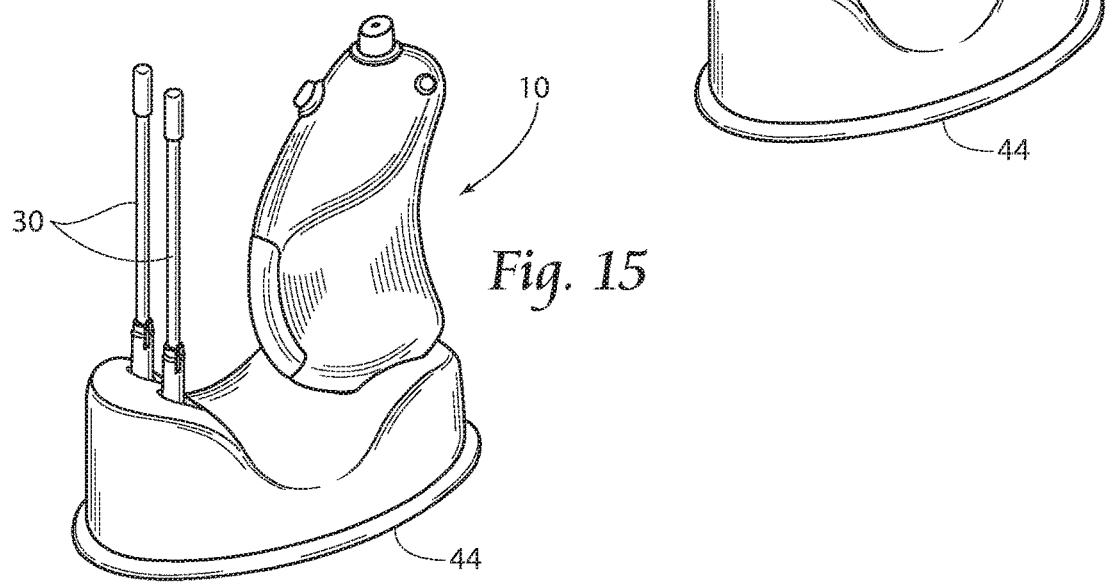
FIG. 15 is a perspective view of the improved hand-held instrument and removable cartridges according to the present invention stored in the base.

FIGS. 14 and 15 depict an optimal base 44 for the storage of the ergonomic hand-held instrument 10 as well as at least one cartridge assembly 30. The base 44 is designed to rest on a flat surface such as a desk, counter or similar work surface.

The improved ergonomic hand-held instrument 10 can be of any suitable dimensions consistent with the above relationships. The instrument 10 can be scaled up or down so as to provide different instruments of different sizes which can thereby accommodate users with different size hands. The instrument of the present invention can be made of any material suitable for the intended purpose of the instrument. Examples include various plastic materials, metals and woods. It should also be noted that the outer surface 64 of the clam shell housing 60 of the device provides a relatively smooth surface which is well-suited for application of art work, logos and advertising. While the embodiment described above is specially designed for a right-handed user, it is to be understood that a similar instrument for a left-handed user is within the purview of the present invention, as shown in FIG. 19.

Figure 16:
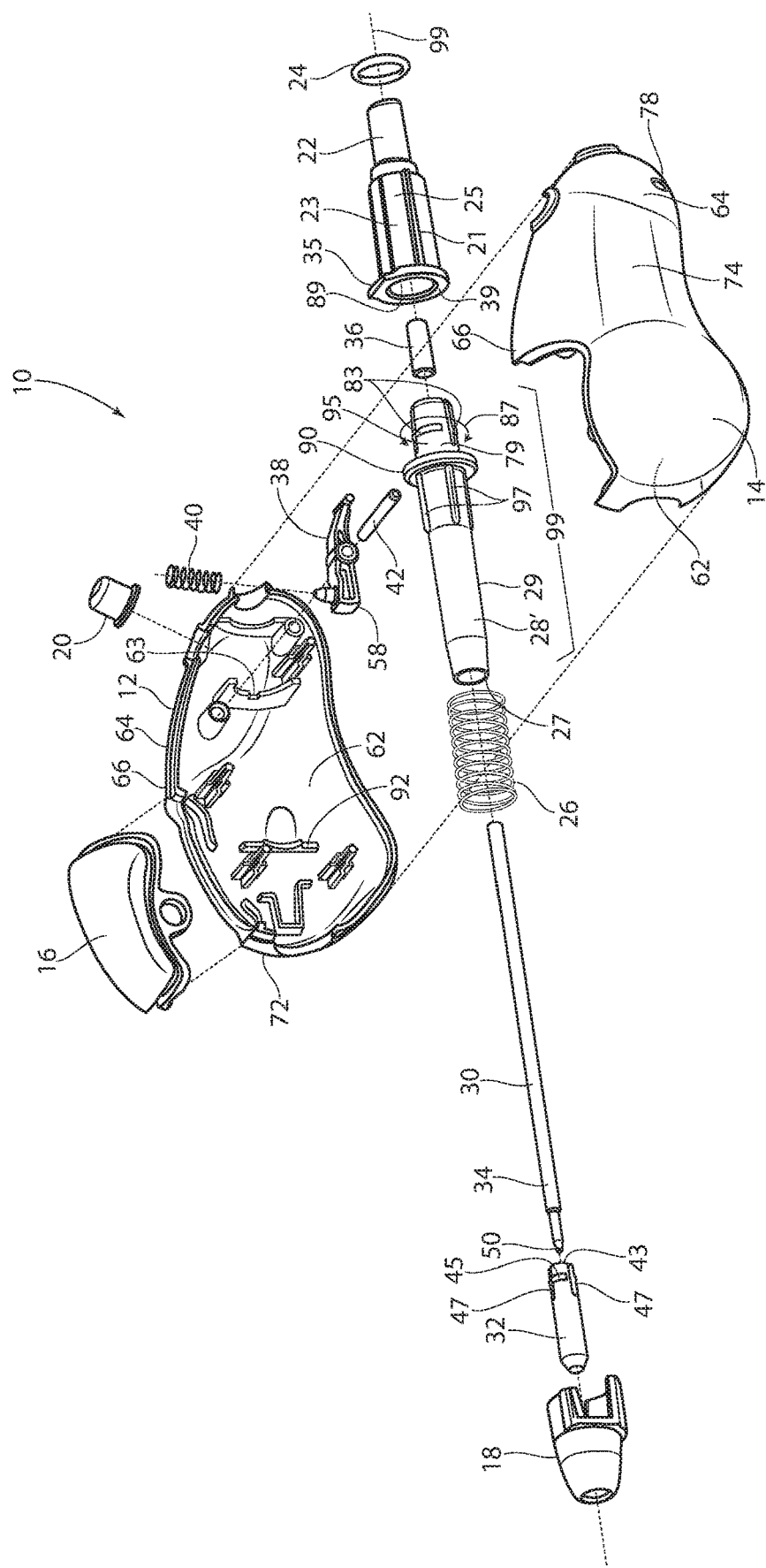
FIG. 16 is an exploded view of the first embodiment of the improved hand-held instrument according to the present invention, further comprising a second embodiment of a cartridge adaptor.
Figure 17:
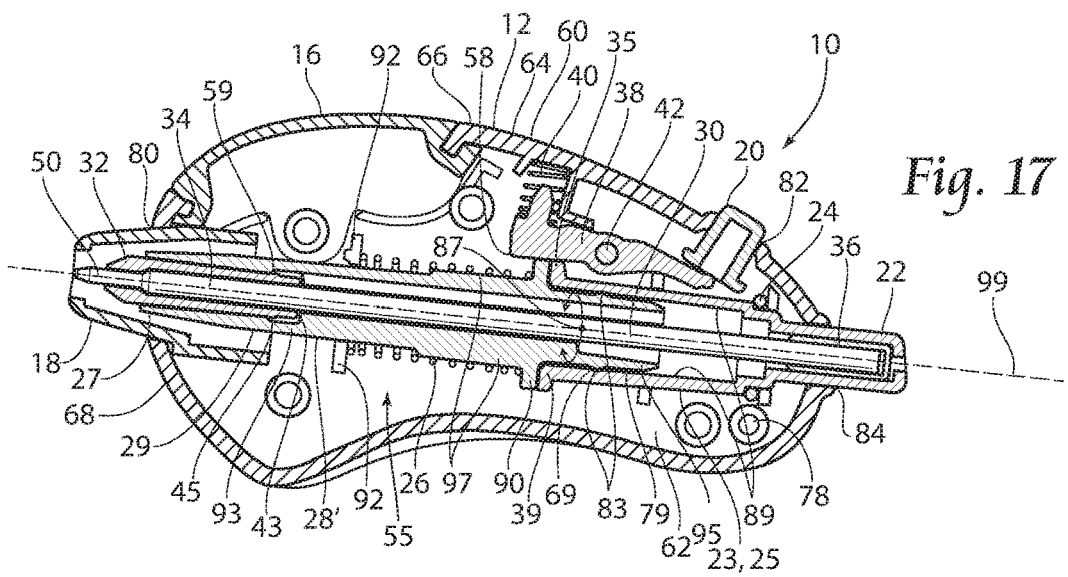
FIG. 17 is a sectional view of the improved hand-held instrument, further comprising the second embodiment of the cartridge adaptor, with the working tool or tip retracted.
Figure 18:
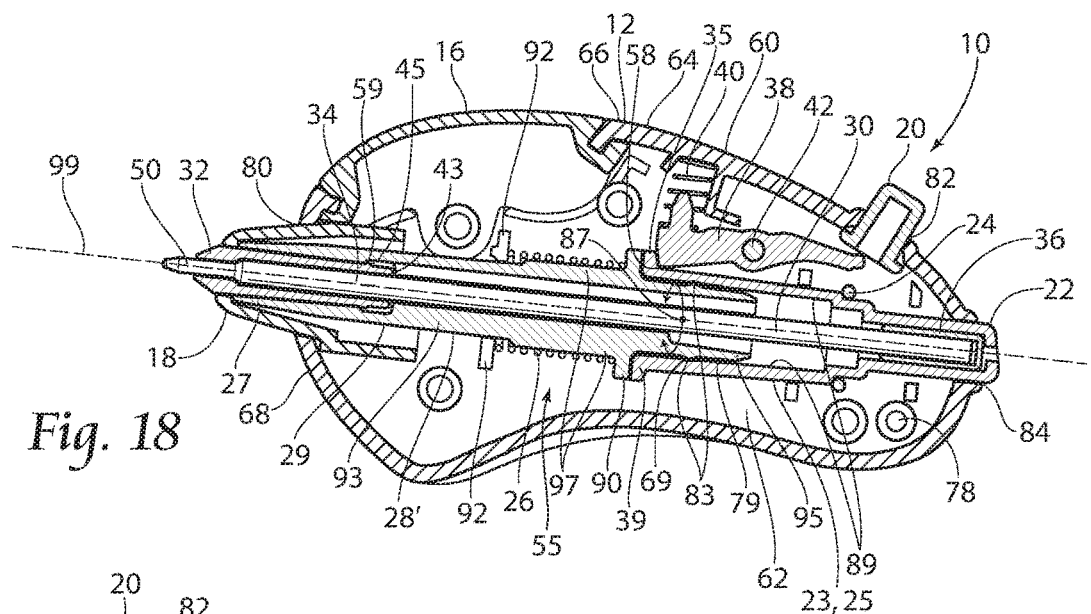
FIG. 18 is a sectional view of the improved hand-held instrument, further comprising the second embodiment of a cartridge adaptor, with the working tool or tip extended.
Figure 19:
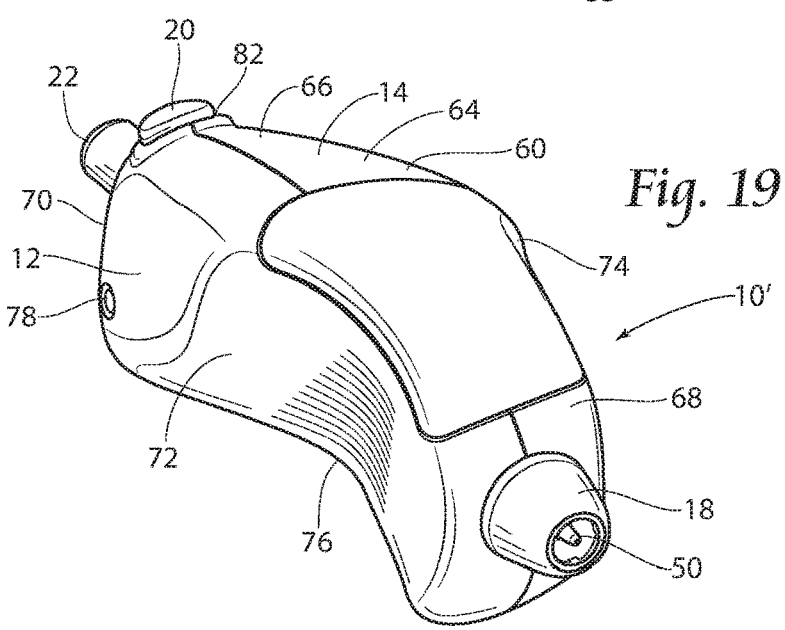
FIG. 19 is a perspective view of a second embodiment of an improved hand-held instrument, according to the present invention with the working tool or tip retracted.

Now referring to FIGS. 16 to 18, the improved ergonomic hand-held instrument 10, as previously described, comprises a second embodiment of the cartridge adaptor 28', which replaces the first embodiment of the cartridge adaptor 28. The second embodiment of the cartridge adaptor 28' incorporates at least one feature of the first embodiment of the cartridge adaptor 28. The second embodiment of the cartridge adaptor 28' further comprises at least one, preferably four, longitudinal ridge 97 along a cartridge adaptor proximal section outer surface 29. The longitudinal ridge 97 extends from the circumferential rib 90 proximally in the direction of a proximal end of the cartridge adaptor 27. Alternatively, the longitudinal ridge 97 may commence in close proximity to the circumferential rib 90. Wherein the longitudinal ridge 97 ends distally with respect, or prior, to the abutment 92 when the cartridge adaptor 28' is installed in the instrument 10.

As illustrated in FIGS. 17 and 18, the longitudinal ridge 97 frictionally contacts the coil spring 26 to reduce lateral movement of the coil spring 26, where lateral movement is orthogonal to, or intersecting, the axis of the cartridge adaptor 99. In doing so, the longitudinal ridge 97 reduces secondary noises which may occur when the instrument 10 is in use. Specifically, the longitudinal ridge provides frictional communication with the concentric coil spring 26, reducing, or minimizing, resonance of the concentric coil spring 26 during extension of the working tool 50 of the cartridge 30 beyond the forward surface 68 of the ergonomically shaped clam shell housing 60. The longitudinal ridge 97 further assists in maintaining the tool or tip 50 in the retracted position.

With further attention to FIGS. 10, 11, 16, 17 and 18, a tip guide distal end 43 is further explained. As illustrated in FIG. 16, the tip guide distal end 43 comprises at least one, preferably three, distal raised ribs 45. Three slots 47 are interspaced between the distal raised ribs 45. The slots 47 extend proximally from the distal end 43. The slots 47 allow for compression of the distal end 43. As illustrated in FIG. 12, compression of the distal end 43 allows for removal of the tip guide 32 during ejection of the cartridge 30. As illustrated in FIGS. 10, 11, 17 and 18, when the guide tip 32 is positioned about the cartridge 30 and within the adaptor (28, 28'), the distal raised ribs 45 contact an internal radial ledge 59 of the adaptor (28, 28'). The contact between the distal raised ribs 45 and the internal radial ledge 59 creates a positional break, arresting movement of the guide tip 32 out of the clam shell 60.

The cartridge adaptor distal section 95 further comprises at least one circumferential ridge 83 extending from distal section outer surface 79. The ridge 83 preferably extends a predetermined length about outer surface 79 which is less than an outer surface circumference 87. Alternatively, the ridge 83 preferably extends a predetermined length about outer surface 79 which is equal to or greater than the outer surface circumference 87.

As previously observed, the cartridge adaptor 28' is nestled within the advance button 22. When in communication, an advance button inner surface 89 contacts the outer surface 79. An advance button inner surface annular groove 69 is provided for in the inner surface 89. When the cartridge adaptor 28' is nestled within the advance button 22, the ridge 83 rests within the annular groove 69. Placement of the ridge 83 in the annular groove 69 provides for a removable coupling between the cartridge adaptor 28' and the advance button 22, maintaining the two in communication with one another during operation of the instrument 10.

With further attention to FIG. 16, the advance button 22 comprises at least one longitudinal rib 21 extending along an outer advance button surface 23 of a main barrel section 25 of the advance button 22. Preferably, the advance button 22 comprises two longitudinal ribs 21 diametrically opposed on the outer advance button surface 23. Each longitudinal rib 21 removably rests in a mating groove 63 positioned on the inner surface 62 of one of the right clam shell housing 12 and the left clam shell housing 14. With the opposite longitudinal rib 21 in connection with groove 63 on the other clam shell housing (12, 14). The mating of each rib 21 with the respective groove 63 rotationally stabilizes the advance button 22. The rotational stabilization of the advance button 22 provides for the release ledge 35 positioned at a proximal end of the advance button 39 to frictionally and reliably contact the release latch 38 in order to position the cartridge assembly 30 in an extended position as seen in FIGS. 10 and 18.

It is observed the housing 60 of the first embodiment of the hand-held instrument 10 provides for a right-handed grip.

Now referring to FIG. 19, a second embodiment of the hand-held instrument 10' is illustrated. The second embodiment of the hand-held instrument 10' incorporates at least one feature of the first embodiment of the hand-held instrument 10. The first embodiment of the hand-held instrument 10 incorporates at least one feature of the second embodiment of the hand-held instrument 10'. The second embodiment of the hand-held instrument 10' provides for a left-handed grip. Thus, the first or right clam shell housing 12, and the second or left clam shell housing 14, of the housing 60 of the second embodiment of the hand-held instrument 10' provide surface features accommodating a left-handed grip.

While there is shown and described herein certain specific structures of this invention for the purpose of clarity of understanding, the same is to be considered as illustrative in character, it being understood that only preferred embodiments have been shown and described. It will be manifest to those skilled in the art that certain changes, various modifications and rearrangements of the parts may be made without departing from the spirit and scope of the underlying inventive concept and claims and that the same is not limited to the particular forms herein shown and described.

I claim:

1. An ergonomic hand-held instrument, comprising:
   a shell having an asymmetric shaped shell body defined by a front and an opposed rear, said shell defining a cavity said front and rear each having an opening;
   a convex top positioned from said front to said rear;
   a longitudinal axis running from said front to said rear, said front opening and rear opening located along said longitudinal axis
   two oppositely opposed sides positioned between said front and said rear; and
   a removable cartridge secured at least partially within said cavity along said longitudinal axis, said cartridge comprising a device tip located outside of said front, said device tip movable from a retracted position to an extended position;
   an advance button located on said rear to maintain the device tip in said extended position;
   an opening located in said advance button accessible to said cavity;
   wherein said cartridge is removed from said cavity by the application of an external force on said cartridge through said opening in said advance button.

2. The ergonomic hand-held instrument of claim 1, wherein said convex top comprising a compression surface in communication with said shell body, wherein said compression surface having a hardness less than said shell body.

3. The ergonomic hand-held instrument of claim 2, wherein said compression surface providing for placement of an index finger.

4. The ergonomic hand-held instrument of claim 1, further comprising a guide tip about said cartridge and frictionally supported and locked within said cavity.

5. The ergonomic hand-held instrument of claim 1, wherein said cartridge is slidably positionable at least partially beyond said rear, through said rear opening.

6. The ergonomic hand-held instrument of claim 5, wherein said cartridge is slidably positionable beyond said front, through said front opening.

7. The ergonomic hand-held instrument of claim 5, wherein said cartridge is an interchangeable cartridge.

8. The ergonomic hand-held instrument of claim 6, wherein said interchangeable cartridge is a quick-change cartridge.

9. The ergonomic hand-held instrument of claim 1, further comprising an o-ring about said cartridge providing for an impact dampening upon cartridge return.

10. The ergonomic hand-held instrument of claim 1, wherein said cartridge is positioned within a cartridge container.

11. The ergonomic hand-held instrument of claim 10, wherein said cartridge container has at least one ridge along a cartridge container outer surface, wherein said ridge frictionally minimizes a resonance of a concentric spring, maintaining a lateral position of said spring.

12. The ergonomic hand-held instrument of claim 10, wherein said cartridge container is rotationally positioned to provide for an extension of said device tip.

13. The ergonomic hand-held instrument of claim 1, wherein said device tip comprises at least one of a pen, a pencil, a stylus and a cutting tool.

14. The ergonomic hand-held instrument of claim 1, wherein a retraction button is positioned through said shell to provide for a retraction of said device tip.

15. An ergonomic hand-held instrument, comprising:
   a shell having an asymmetrical shell body defined by a front and an opposed rear, each of said front and said rear having an opening, said shell defining a cavity;
   a convex top positioned from said front to said rear, said convex top comprising a compression surface in communication with said shell body, wherein said compression surface having a hardness less than said shell body;
   a longitudinal axis running from said front to said rear, said front opening and rear opening located along said longitudinal axis
   two oppositely opposed sides positioned between said front and said rear; and
   a removable, interchangeable cartridge secured at least partially within said cavity along said longitudinal axis, stud cartridge comprising a device tip located outside of said front, said device tip movable from a retracted position to an extended position;
   an advance button located on said rear to maintain the device tip in said extended position;
   an opening located in said advance button accessible to said cavity;
   wherein said cartridge is removed from said cavity by the application of an external inserted probe force on said cartridge through said opening in said rear; and
   a retraction button located on said shell, said retraction button moving said device tip from said extended position to said retracted position.

16. An ergonomic hand-held instrument, comprising:
   a shell having an asymmetrical shell body defined by a front and an opposed rear, each of said front and said rear having an opening, said shell defining a cavity;

a convex top positioned from said front to said rear, said convex top comprising a compression surface in communication with said shell body, wherein said compression surface having a hardness less than said shell body;

a longitudinal axis running from said front to said rear, said front opening and rear opening located along said longitudinal axis; and a removable, interchangeable cartridge secured at least partially within said cavity along said longitudinal axis, said cartridge comprising a device tip located outside of said front, said device tip movable from a retracted position to an extended position;

an O-ring located about said cartridge to dampen the impact of the cartridge when moving from said extended position to said retracted position;

an advance button located on said rear to maintain the device tip in said extended position;

an opening located in said advance button accessible to said cavity;

wherein said cartridge is removed from said cavity by the application of an external inserted probe force on said cartridge through said opening in said rear; and a retraction button located on said shell, said retraction button moving said device tip from said extended position to said retracted position.

* * * * *